(12) United States Patent
Wu et al.

(10) Patent No.: US 12,179,207 B2
(45) Date of Patent: Dec. 31, 2024

(54) DIGITAL PCR SYSTEM AND DIGITAL PCR DROPLET FORMATION METHOD

(71) Applicant: SHANGHAI INDUSTRIAL μTECHNOLOGY RESEARCH INSTITUTE, Shanghai (CN)

(72) Inventors: Xuanye Wu, Shanghai (CN); Yimin Guan, Shanghai (CN)

(73) Assignee: SHANGHAI INDUSTRIAL μ TECHNOLOGY RESEARCH INSTITUTE, Shanghai (CN)

( * ) Notice: Subject to any disclaimer, the term of this patent is extended or adjusted under 35 U.S.C. 154(b) by 983 days.

(21) Appl. No.: 17/044,500

(22) PCT Filed: Nov. 23, 2018

(86) PCT No.: PCT/CN2018/117310
§ 371 (c)(1),
(2) Date: Feb. 16, 2021

(87) PCT Pub. No.: WO2020/034482
PCT Pub. Date: Feb. 20, 2020

(65) Prior Publication Data
US 2021/0220831 A1  Jul. 22, 2021

(30) Foreign Application Priority Data
Aug. 13, 2018  (CN) .......................... 201810916910.2

(51) Int. Cl.
*B01L 3/00* (2006.01)
*B01L 7/00* (2006.01)
*C12Q 1/686* (2018.01)

(52) U.S. Cl.
CPC ................. *B01L 7/52* (2013.01); *C12Q 1/686* (2013.01); *B01L 2300/041* (2013.01); *B01L 2300/0816* (2013.01); *B01L 2300/1827* (2013.01)

(58) Field of Classification Search
None
See application file for complete search history.

(56) References Cited

U.S. PATENT DOCUMENTS 11,326,200 B2 *  5/2022  Cumbie ................. B01L 3/5088
11,911,731 B2 *  2/2024  Torniainen .............. B01F 23/41
(Continued)

FOREIGN PATENT DOCUMENTS

CN    104046556 A2    9/2014
CN    104487592 A     4/2015
(Continued)

*Primary Examiner* — Brian R Gordon
(74) *Attorney, Agent, or Firm* — NKL Law; Allen Xue

(57) ABSTRACT

A digital PCR system includes a droplet formation assembly and a droplet ejection hole assembly, the droplet ejection hole assembly being connected below the droplet formation assembly. The droplet formation assembly includes a cover plate and at least one annular step connected to a lower surface of the cover plate, and the droplet ejection hole assembly has a plurality of droplet ejection holes. The upper surface of the droplet ejection hole assembly, the lower surface of the cover plate and the annular step jointly enclose to form a droplet formation chamber. A vaporization component is provided within the droplet ejection holes, being used for vaporizing a liquid layer of a digital PCR solution in the droplet ejection holes and quickly pushing same into droplet formation oil in the droplet formation chamber so as to form digital PCR droplets.

18 Claims, 13 Drawing Sheets

(56) References Cited

U.S. PATENT DOCUMENTS

| | | | | |
|---|---|---|---|---|
| 2002/0045272 | A1* | 4/2002 | McDevitt | B01L 3/502761 |
| | | | | 436/518 |
| 2002/0160363 | A1* | 10/2002 | McDevitt | G01N 33/54326 |
| | | | | 436/526 |
| 2010/0190263 | A1* | 7/2010 | Srinivasan | B01F 33/3031 |
| | | | | 422/534 |
| 2012/0236299 | A1* | 9/2012 | Chiou | G01N 29/2418 |
| | | | | 239/10 |
| 2013/0217103 | A1* | 8/2013 | Bauer | G01N 27/44791 |
| | | | | 422/501 |
| 2014/0174926 | A1* | 6/2014 | Bort | B01F 33/3021 |
| | | | | 204/601 |
| 2015/0212043 | A1* | 7/2015 | Pollack | B01L 3/502792 |
| | | | | 204/601 |
| 2018/0298318 | A1* | 10/2018 | Kurz | C12M 23/20 |
| 2021/0238434 | A1* | 8/2021 | Kozee | C09D 11/36 |
| 2023/0285970 | A1* | 9/2023 | Shkolnikov | B01L 3/0268 |

FOREIGN PATENT DOCUMENTS

| | | |
|---|---|---|
| CN | 104611223 A | 5/2015 |
| CN | 106520524 A | 3/2017 |
| CN | 106754341 A | 5/2017 |
| CN | 106824313 A | 6/2017 |
| CN | 106834115 A | 6/2017 |

\* cited by examiner

DIGITAL PCR SYSTEM AND DIGITAL PCR DROPLET FORMATION METHOD

TECHNICAL FIELD

The present invention belongs to the field of biomedicine, in particular to the field of disease diagnostics, and relates to an integrated in situ digital PCR system and a method for generating digital PCR droplets.

BACKGROUND ART

Polymerase chain reaction (PCR) has been proposed for 20 years, during which PCR has developed into a key and conventional technique in the area of molecular biology, greatly promoting the development of various areas of life sciences. In particular, in the late 1990s, ABI in the United States not only introduced the real-time fluorescent quantitative PCR (real time PCR, qPCR) technique and related products, but also developed PCR from a technique for in-vitro synthesis and qualitative/semi-quantitative detection into a highly sensitive, highly specific and accurate quantitative technique for gene analysis.

Despite rapid development more than 10 years, qPCR technique has been used for diagnosis of all diseases except injuries and nutrient deficiencies. However, the PCR amplification efficiency is affected by many factors during amplification. It cannot ensure the same amplification efficiency during reaction, or between the actual samples and the standard samples, and among various samples. Thus, the cycle threshold (CT) value which is the basis of quantitative analysis, is not constant. Therefore, the quantification of qPCR is only "relative quantification", and its accuracy and reproducibility still cannot meet the requirements of quantitative analysis in molecular biology.

At the end of the 20th century, Vogelstein et al. proposed the concept of a digital PCR (dPCR), which involved distributing a sample into tens to tens of thousands of parts to different reaction units. Each unit contained one or a few copies of a target molecule (Template DNA). In each reaction unit, the target molecule was amplified by PCR, and the fluorescence signal of each reaction unit was statistically analyzed after completion of the amplification reaction. Unlike qPCR, digital PCR did not depend on CT values, so it was not affected by amplification efficiency. After completion of the amplification reaction, the average concentration (content) in each reaction unit was calculated by directly counting or using the Poisson distribution equation, and the error could be controlled within 5%. Digital PCR enabled the absolute quantitative analysis without the need for standard samples and curves.

Digital PCR (also known as a single molecule PCR) generally comprises two parts, i.e. PCR amplification and fluorescence signal analysis. At the PCR amplification stage, unlike traditional techniques, samples in digital PCR are generally required to be diluted to the level of single molecules and evenly distributed into tens to tens of thousands of units for reaction. Unlike qPCR, which measures real-time fluorescence at each cycle, the digital PCR technique collects the fluorescence signal in each reaction unit after amplification. Finally, the original concentrations or contents of the samples are calculated by directly counting or using the Poisson distribution equation.

Since digital PCR is a technique for absolute quantification of nucleic acid molecules, and compared with qPCR, it can directly count the number of DNA molecules, which is to absolutely quantify starting samples, digital PCR is especially suitable for application fields where it cannot be well distinguished from CT values, such as copy number variation, mutation detection, relative gene expression studies (e.g., allelic imbalance gene expression), validating second-generation sequencing, miRNA expression analysis, single-cell gene expression analysis etc.

At present, there are three main types of digital PCR techniques on the market. One is to generate droplets by shearing an aqueous PCR solution with flowing oil in a specific apparatus, and then complete PCR and detection in other two apparatuses; another one is to distribute a PCR solution onto a hollow silicon wafer, then perform PCR in a specific apparatus and detect in another apparatus; the last one is to generate droplets by injecting a liquid into a chamber through a narrow channel in one apparatus and complete PCR, and then complete detection in another apparatus. However, the current three methods have limitations on the flux or the rate of droplet generation. Furthermore, the above three techniques rely on multiple large apparatuses without exception. This not only increases the purchase cost of apparatuses and limits the widespread use of digital PCR, but also increases the complexity of experimental operations.

Therefore, it has become an important technical problem to be solved urgently by those skilled in the art, how to provide a technique for high-speed digital PCR droplet generation at a rate of more than 1000 droplets per second, an in-situ PCR technique for integrating droplet generation with PCR temperature control and detection instruments, and a method for an efficient utilization rate of digital PCR oil.

SUMMARY OF THE DISCLOSURE

In view of the above-mentioned disadvantages of the prior art, an object of the present invention is to provide an integrated in situ digital PCR system and a method for generating digital PCR droplets to solve the problems of slow droplet generation rate, small flux, complicated operation and low utilization rate of PCR oil in the prior art.

To achieve the above object and other related objects, the present invention provides a digital PCR system, comprises:

a droplet generation component, comprising a cover plate and at least one annular step connected to the lower surface of the cover plate;

a droplet nozzle member, connected below the droplet generation component and comprising a plurality of droplet nozzles; the droplet nozzles have openings on the upper surface of the droplet nozzle member, and extend toward, but not through, the lower surface of the droplet nozzle member, wherein the upper surface of the droplet nozzle member, the lower surface of the cover plate and the annular step together form a droplet generation chamber, the droplet nozzles are in communication with the droplet generation chamber, and the droplet nozzles have vaporizing parts for vaporizing liquid layers of the digital PCR solution in the droplet nozzles, and rapidly pushing the vaporized liquid into droplet generating oil in the droplet generation chamber to generate digital PCR droplets.

Optionally, the droplet nozzle member comprises a thermal bubble print chip.

Optionally, the height of the annular step is less than twice the diameter of digital PCR droplets to be generated, so that the obtained digital PCR droplets spread out to form a one-layer structure in the droplet generation chamber.

Optionally, the droplet generation component further comprises at least one droplet generating oil injection hole, the droplet generating oil injection hole is in communication with the droplet generation chamber through the cover plate.

Optionally, the droplet generation component further comprises at least one exhaust port of droplet generation chamber, the exhaust port of droplet generation chamber is in communication with the droplet generation chamber through the cover plate.

Optionally, the vaporizing parts are arranged on a lower surface or sidewall of the droplet nozzles.

Optionally, the shape of the opening of the droplet nozzle comprises any one selected from the group consisting of round, ellipse and polygon.

Optionally, the vaporizing parts comprise heating elements for vaporizing liquid layers of the digital PCR solution by heating.

Optionally, the heating elements comprise at least one metal layer.

Optionally, the PCR system further comprises at least one PCR reagent chamber for storing the digital PCR solution, the droplet nozzle member has a flow channel, and the droplet nozzles are in communication with the PCR reagent chamber through the flow channel.

Optionally, the flow channel comprise at least one main flow channel and a plurality of branch flow channels connected to the main flow channel, and each of the droplet nozzles is connected to one of the branch flow channels, respectively.

Optionally, the digital PCR system further comprises a substrate, the PCR reagent chamber has an opening on the upper surface of the substrate, and extends toward, but not through, the lower surface of the substrate, and the droplet nozzle member is connected to the upper surface of the substrate, and covers the opening of the PCR reagent chamber.

Optionally, at least one digital PCR solution injection hole is provided on the lower surface of the substrate, the digital PCR solution injection hole is in communication with the PCR reagent chamber.

Optionally, at least one exhaust port of PCR reagent chamber is provided on the lower surface of the substrate, the exhaust port of PCR reagent chamber is in communication with the PCR reagent chamber.

Optionally, the digital PCR system further comprises a flexible circuit board, the flexible circuit board is connected above the substrate, the flexible circuit board has a through hole for accommodating the droplet nozzle member, a plurality of the first connection pads and the second connection pads are arranged on the surface of the flexible circuit board, and the droplet nozzle member is connected to the first connection pads by conducting wires.

Optionally, the flexible circuit board is connected to the substrate by gluing.

Optionally, the cross-sectional area of the droplet generation component is larger than the area of the opening of the PCR reagent chamber, at least one channel is provided on the region of the substrate surface for preventing glue from flowing to the droplet nozzle member, wherein the region of the substrate surface is covered by the droplet nozzle member.

Optionally, an annular channel is provided on the surface of the substrate for preventing glue from flowing to the droplet nozzle member, the annular channel being arranged around the droplet nozzle member.

Optionally, at least two positioning through holes are arranged in the flexible circuit board, positioning bumps at positions corresponding to the positioning through holes is provided on the surface of the substrate.

Optionally, the digital PCR system further comprises a controller, the controller comprises a controller housing and a controller circuit board arranged in the controller housing, the controller housing has a support for placing the substrate, a plurality of conductive pins for circuit connection connected to the circuit connection board of the controller are arranged on the surface of the support, and the conductive pins for circuit connection are at positions corresponding to the second connection pads.

Optionally, at least one position-limiting slot is provided at one end of the substrate, and the controller housing has at least one position-limiting part corresponding to the position-limiting slot.

Optionally, the substrate has a position-limiting through hole, the position-limiting through hole penetrates the front surface and the back surface of the substrate, and the controller housing has a position-limiting part corresponding to the position-limiting slot.

Optionally, the controller further comprises a cover, the cover is connected to the controller housing and is used to cover the substrate.

Optionally, the digital PCR system further comprises a heating module for heating the droplet generation chamber.

Optionally, the heating module is integrated in the droplet nozzle member.

Optionally, the digital PCR system further comprises an external cooling fan for cooling the droplet generation chamber.

Optionally, the digital PCR system further comprises an external thermoelectric cooler for cooling the droplet generation chamber.

Optionally, the digital PCR system also comprises a temperature sensor for measuring temperature of the droplet generation chamber.

Optionally, the temperature sensor is integrated in the droplet nozzle member.

Optionally, the digital PCR system further comprises an optical detection system for PCR signal collection and detection without transferring samples.

The present invention also provides a method for generating digital PCR droplets, comprising the following steps of:

injecting digital PCR solution into a PCR reagent chamber, so that the digital PCR solution enters droplet nozzles in communication with the PCR reagent chamber to form liquid layers;

adding droplet generating oil into the droplet generation chamber;

the liquid layers are vaporized by using the vaporizing parts and rapidly pushed into the droplet generating oil in the droplet generation chamber to generate the digital PCR droplets.

Optionally, the vaporizing parts comprise heating elements for vaporizing the liquid layers by heating.

Optionally, a generation rate of the digital PCR droplets is controlled by controlling the heating time, the number of heatings and the time intervals of heating of the heating elements.

Optionally, the thickness of the liquid layer is in the range from 0.2 nm to 30,000 nm.

Optionally, the height of the droplet generation chamber is less than twice the diameter of digital PCR droplets to be generated, so that the obtained digital PCR droplets spread out to form a one-layer structure in the droplet generation chamber.

Optionally, the digital PCR droplets are generated at a rate of more than 1000 droplets per second.

As described above, the digital PCR system and the method for generating digital PCR droplets of the present invention have the following beneficial effects:

(1) Thermal bubble technique is used in the present invention for high-speed digital PCR droplet generation. The rapid droplet generation relies on the instantaneous heating and vaporization of liquid layers with a thickness in nanometer-scale by using vaporizing parts in droplet nozzles, so that digital PCR solution inside the droplet nozzles is quickly pushed into droplet generating oil to generate digital PCR droplets. Compared with the generation rate of 100 droplets per second on the market, a droplet generation speed of more than 1000 drops per second can be achieved by the droplet generation technique of the present invention.

(2) Compared with the method by which the oil and water phases move together to generate droplets, the oil phase in the technical solution of the present invention is static, so the consumption of oil is greatly reduced, reducing the amount of oil by about 50%.

(3) Because of the precise temperature control integrated on the silicon-based droplet nozzle member or thermal bubble printing chips, in situ temperature-controlled PCR is realized. And the integrated optical system allows detection without transferring samples. This not only reduces the operation time, but also improves the accuracy of detection by reducing human error.

(4) In situ digital PCR droplets may spread out to form a one-layer structure.

Figure 1:
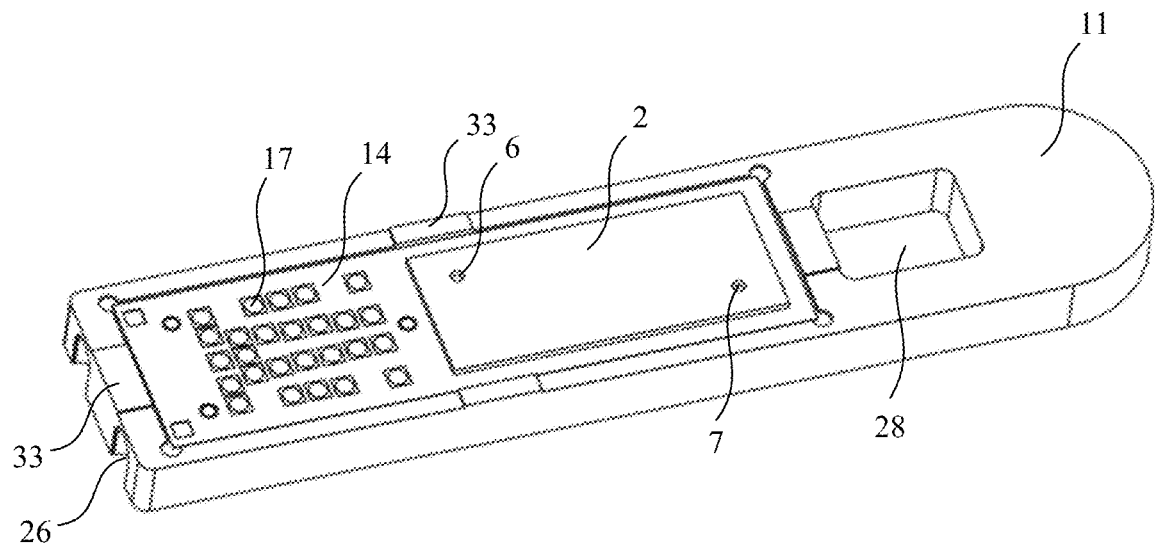
FIG. 1 is a perspective view of the digital PCR system of the present invention.

LIST OF REFERENCE NUMERALS 1 droplet generation component
2 cover plate
3 annular step
4 droplet nozzle member
5 droplet nozzle
6 droplet generating oil injection hole
7 exhaust port of droplet generation chamber
8 PCR reagent chamber
9 main flow channel
10 branch flow channel
11 substrate
12 digital PCR solution injection hole
13 exhaust port of PCR reagent chamber
14 flexible circuit board
15 through hole
16 housing supporting structure
17 second connection pad
18 channel
19 annular channel
20 positioning through hole
21 positioning bump
22 controller
23 controller housing
24 support
25 conductive pin for circuit connection
26 position-limiting slot
27, 29 position-limiting part 28 position-limiting through hole
30 cover
31 external cooling fan
32 sunken platform
33 protrusion
34 vent
35 connection point of circuit board
36 droplet generation chamber

DETAILED DESCRIPTION OF THE INVENTION

Hereinafter, the embodiments of the present invention will be illustrated with specific examples, and other advantages and benefits of the present invention can be readily understood by those skilled in the art as disclosed in this specification. The present invention may also be implemented or applied with various other specific embodiments, and the details in this specification may be modified or altered in various ways based on different points of view and applications without departing from the spirit of the present invention.

Referring to FIG. 1 to FIG. 40. It should be noted that the illustrations provided in the examples only illustrate the basic concept of the present invention in a schematic manner, and that the drawings only show the components related to the present invention rather than the numbers, shapes and sizes of the components in actual implementation, and that the shape, number and ratio of each component in actual implementation may be changed arbitrarily, and the types of layout pattern of the components may be also more complicated.

Embodiment 1

Figure 2:
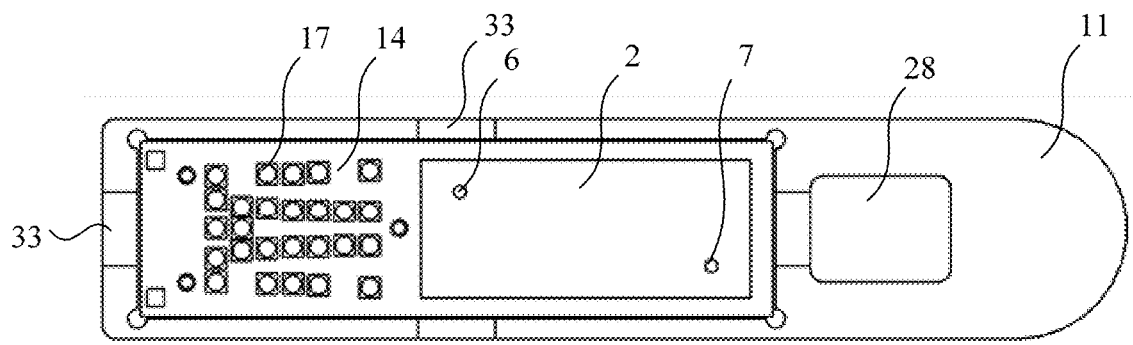
FIG. 2 is a top view of the digital PCR system of the present invention.
Figure 3:
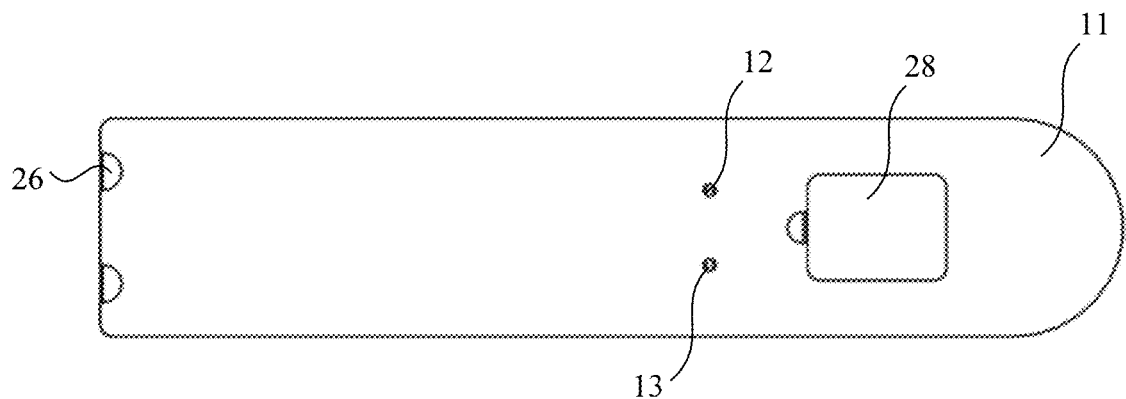
FIG. 3 is a bottom view of the digital PCR system of the present invention.
Figure 4:
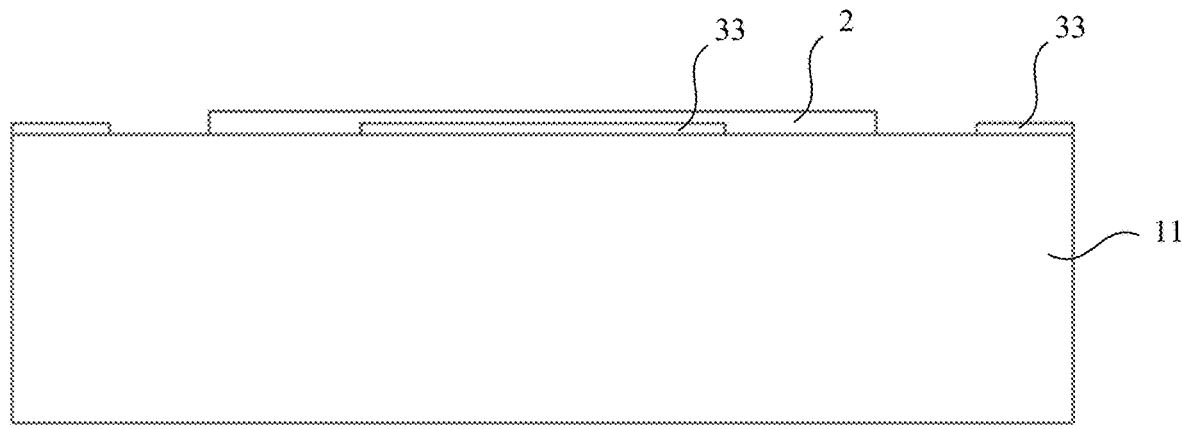
FIG. 4 to FIG. 7 are side views of the digital PCR system.
Figure 5:
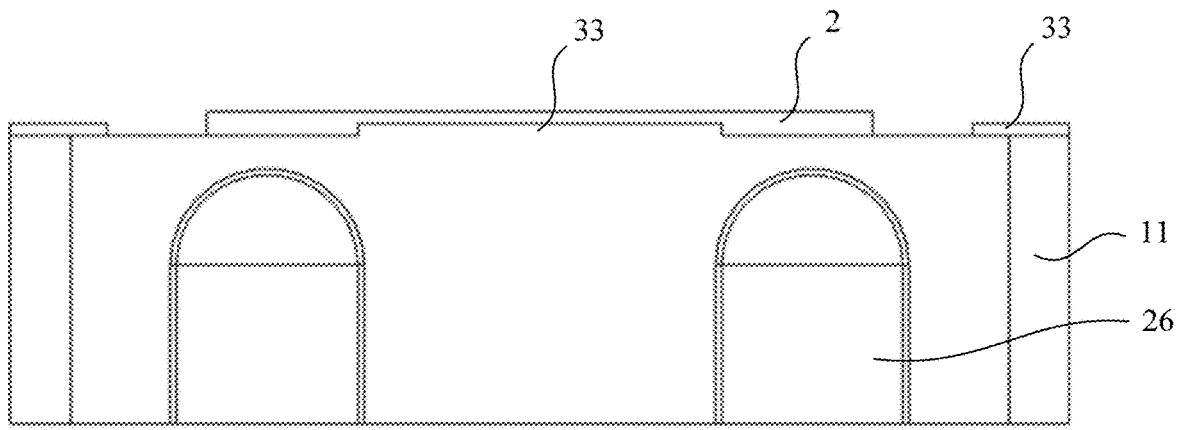
Figure 6:
Figure 7:
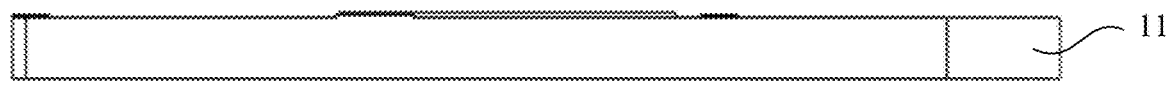

The present invention provides a digital PCR system, as shown in FIG. 1 to FIG. 7, among them, FIG. 1 is a perspective view of the digital PCR system, FIG. 2 displays a top view of the digital PCR system, FIG. 3 shows a bottom view of the digital PCR system, and FIG. 4, FIG. 5, FIG. 6, and FIG. 7 are side views of the digital PCR system in four directions.

Figure 8:
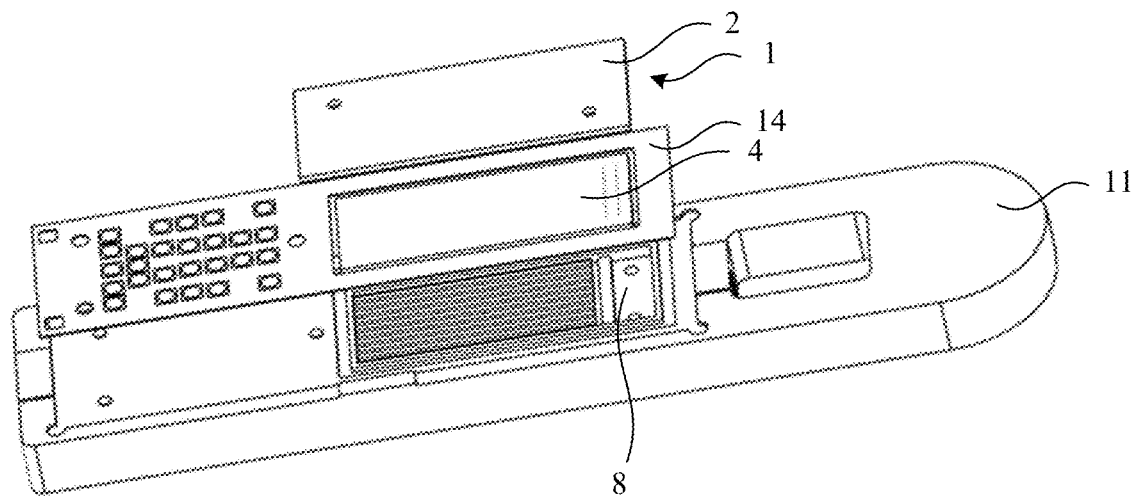
FIG. 8 is an exploded view of the digital PCR system of the present invention.

Referring to FIG. 8, it is an exploded view of the digital PCR system, which shows that the digital PCR system comprises a droplet generation component 1 and a droplet nozzle member 4, wherein droplet nozzle member 4 is connected below the droplet generation component 1.

As an example, the droplet nozzle member 4 comprises thermal bubble print chips. Thermal bubble print technique is a major technique in the field of printers, the basic principle of the thermal bubble print technique is to eject ink droplets by heating ink. In the present invention, droplet nozzle member 4 may use existing thermal bubble print chips.

Figure 9:
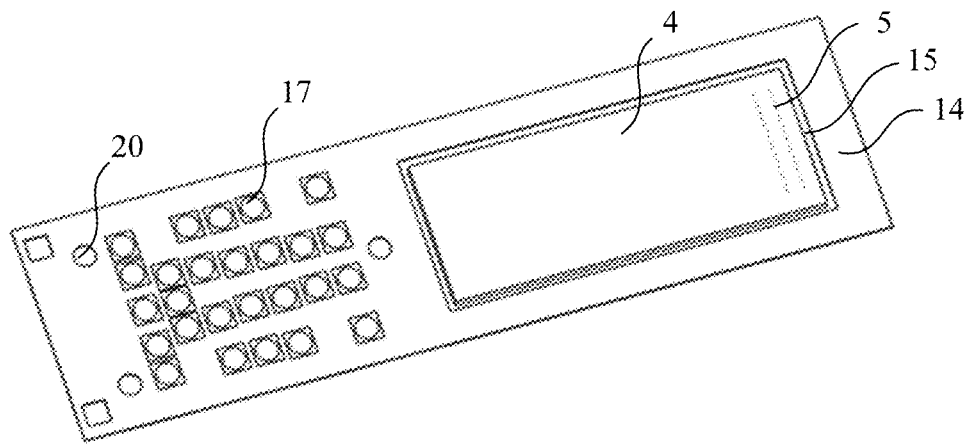
FIG. 9 is a front perspective view of the droplet nozzle member connected to the flexible circuit board in the digital PCR system of the present invention.
Figure 10:
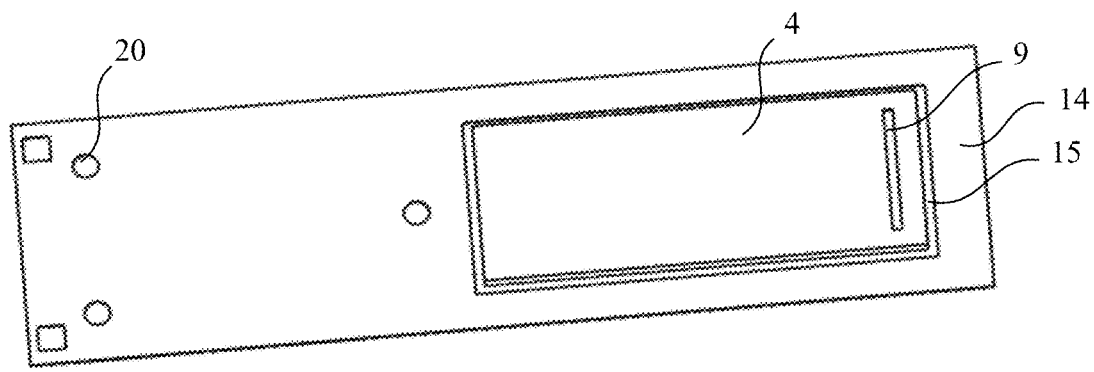
FIG. 10 is a back perspective view of the droplet nozzle member connected to the flexible circuit board in the digital PCR system of the present invention.
Figure 11:
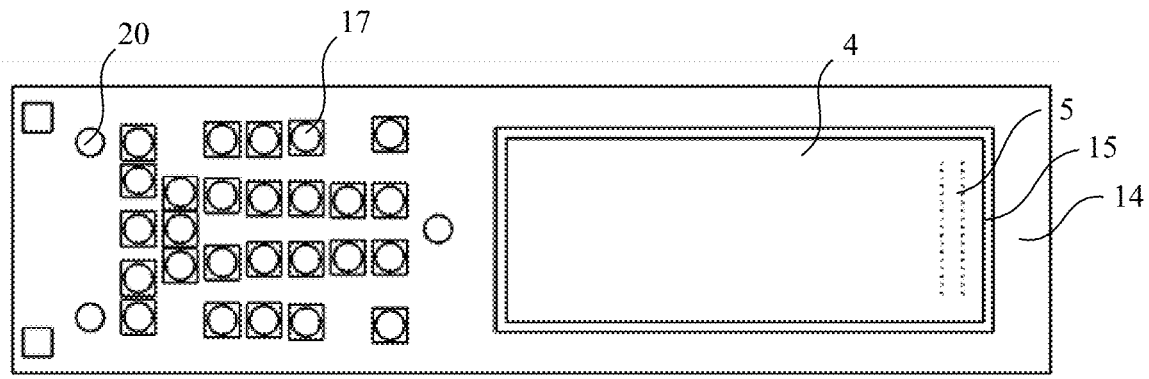
FIG. 11 is a top view of the droplet nozzle member connected to the flexible circuit board in the digital PCR system of the present invention.
Figure 12:
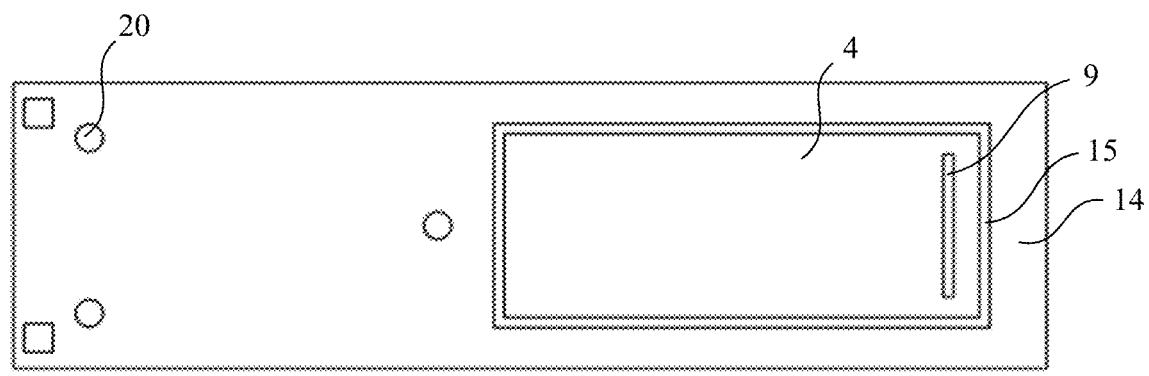
FIG. 12 is a bottom view of the droplet nozzle member connected to the flexible circuit board in the digital PCR system of the present invention.
Figure 13:
FIG. 13 to FIG. 16 are side views of the droplet nozzle member connected to the flexible circuit board in the digital PCR system of the present invention.
Figure 14:
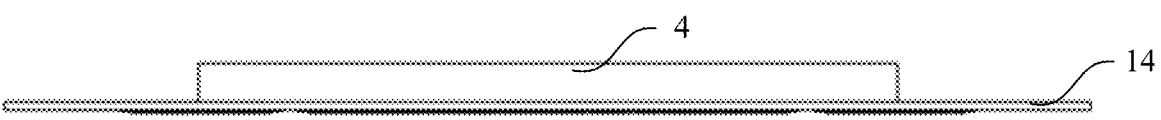
Figure 15:
Figure 16:
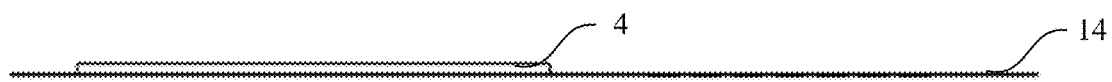

In the present embodiment, the droplet nozzle member 4 is connected to flexible circuit board 14. Referring to FIG. 9 to FIG. 16, wherein, FIG. 9 is a front perspective view of droplet nozzle member 4 connected to flexible circuit board 14; FIG. 10 is a back perspective view of droplet nozzle member 4 connected to flexible circuit board 14; FIG. 11 is a top view of droplet nozzle member 4 connected to flexible circuit board 14; FIG. 12 is a bottom view of droplet nozzle member 4 connected to flexible circuit board 14; and FIG. 13, FIG. 14, FIG. 15 and FIG. 16 are side views of droplet nozzle member 4 connected to flexible circuit board 14 in four directions.

Specifically, a through hole 15 is provided in flexible circuit board 14 for accommodating droplet nozzle member 4, a plurality of the first connection pads (not shown) and the second connection pads 17 are arranged on the surface of the flexible circuit board 14, the droplet nozzle member 4 is connected to the first connection pads by conducting wires, and he droplet nozzle member 4 is connected to an external controller via flexible circuit board 14. The droplet nozzle member 4 is connected to the first connection pads by using a standard Wire Bond process.

Specifically, as shown in FIG. 9 and FIG. 11, the droplet nozzle member 4 comprises a plurality of droplet nozzles 5. In the embodiment, the droplet nozzles 5 are arranged in two rows near one end of droplet nozzle member 4 and the droplet nozzles is evenly distributed in each row. In other embodiments, droplet nozzles 5 may also be arranged in other ways, and the scope of protection of the present invention should not be unduly limited herein.

Figure 17:
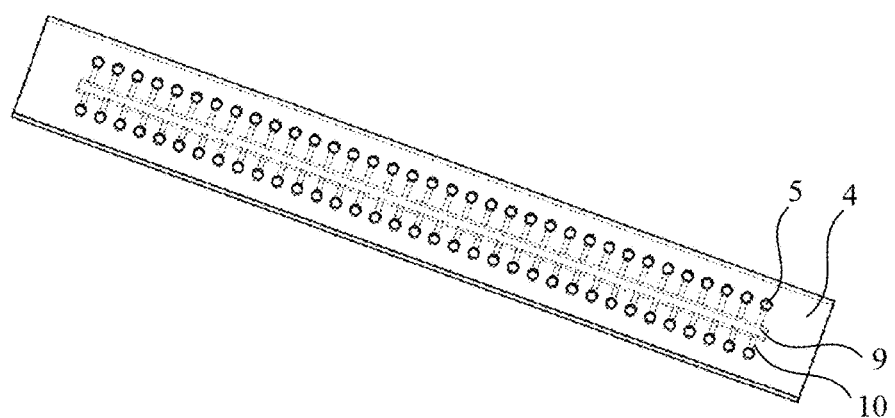
FIG. 17 is a partial perspective view of the droplet nozzle member in the digital PCR system of the present invention.
Figure 18:
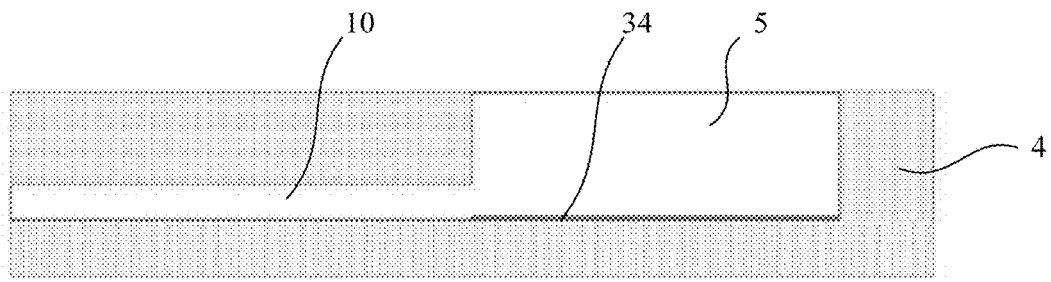
FIG. 18 is a partial cross-sectional view of the droplet nozzle member in the digital PCR system of the present invention.

Referring to FIG. 17 and FIG. 18, wherein, FIG. 17 shows a partial perspective view of the droplet nozzle member 4, and FIG. 18 is a partial cross-sectional view of the droplet nozzle member. It can be seen that droplet nozzles 5 have openings on the upper surface of the droplet nozzle member 4, and extend toward, but not through, the lower surface of the droplet nozzle member 4. The shape of the opening of each of the droplet nozzles 5 comprises, but is not limited to, any one selected from the group consisting of round, ellipse and polygon.

Figure 19:
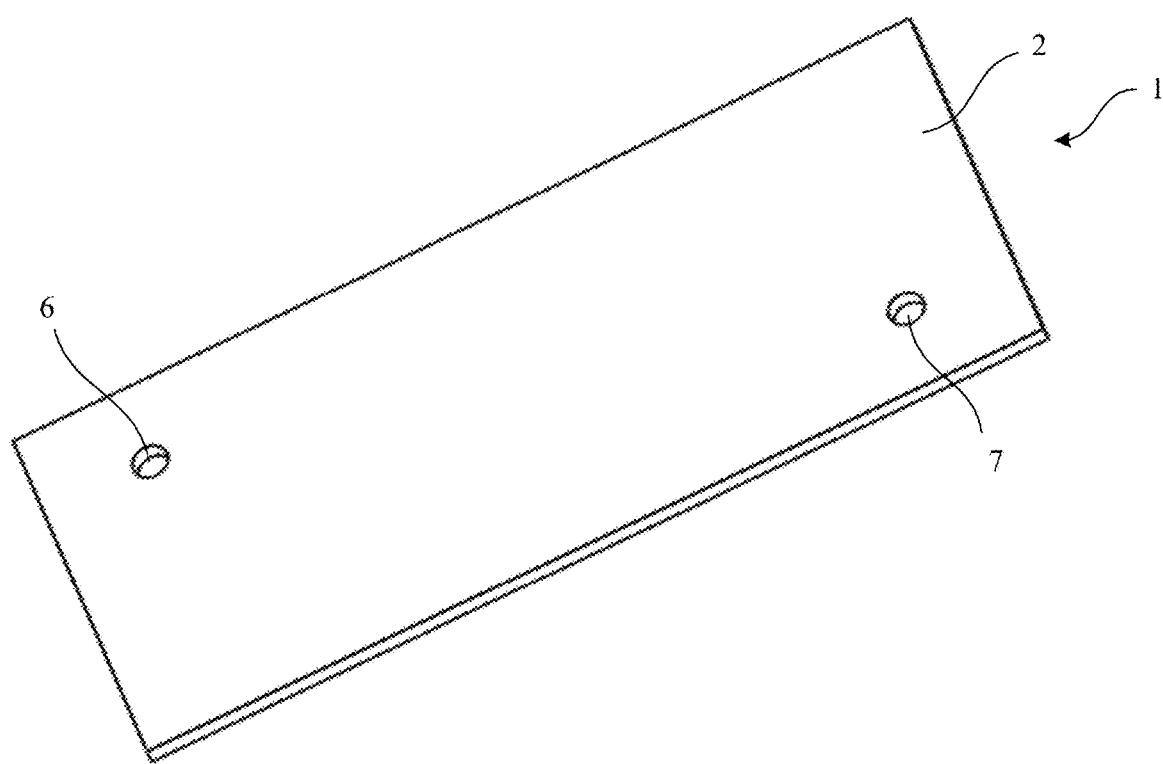
FIG. 19 is a front perspective view of the droplet generation component in the digital PCR system of the present invention.
Figure 20:
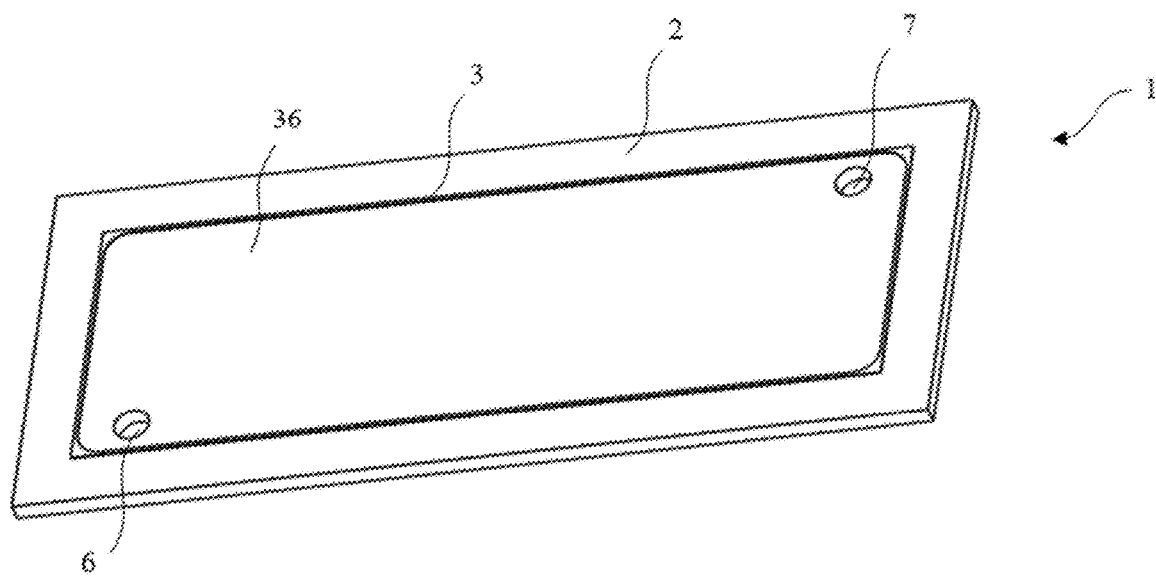
FIG. 20 is a back perspective view of the droplet generation component in the digital PCR system of the present invention.
Figure 21:
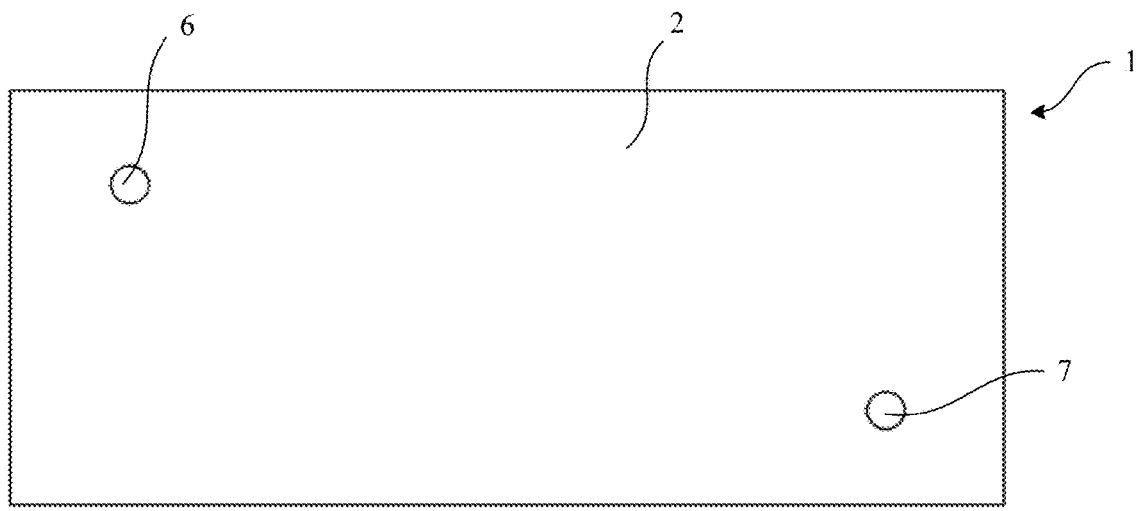
FIG. 21 is a top view of the droplet generation component in the digital PCR system of the present invention.
Figure 22:
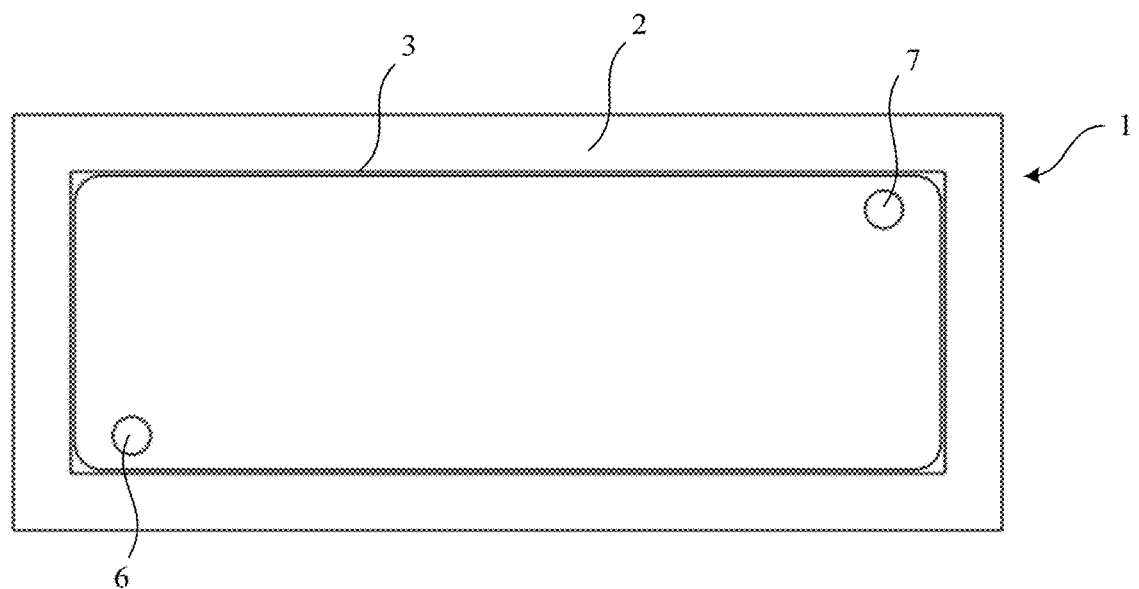
FIG. 22 is a bottom view of the droplet generation component in the digital PCR system of the present invention.
Figure 23:
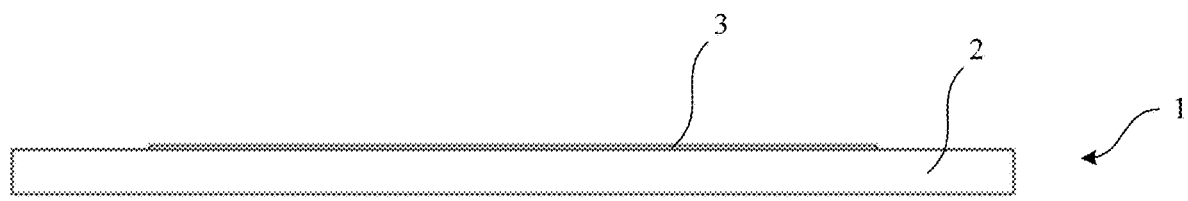
FIG. 23 to FIG. 26 are side views of the droplet generation component in the digital PCR system of the present invention.
Figure 24:
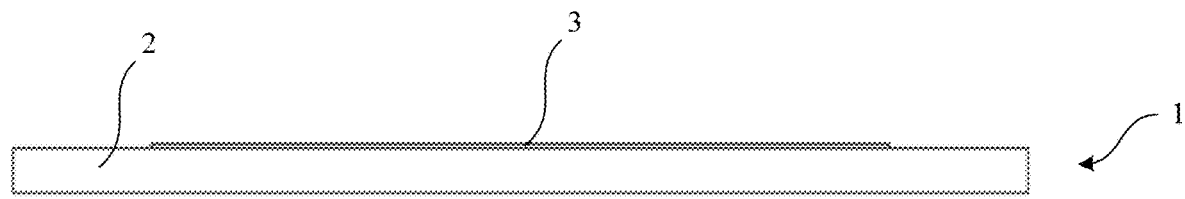
Figure 25:
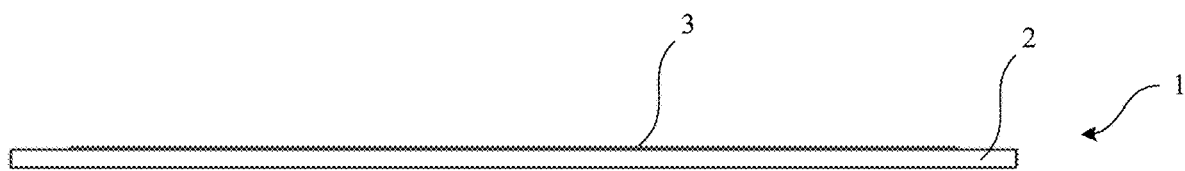
Figure 26:
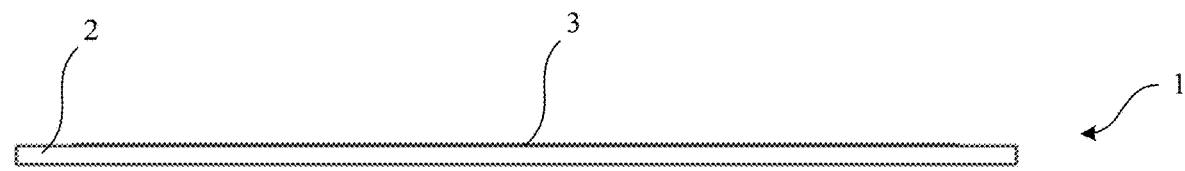

Referring to FIG. 19 to FIG. 26, wherein, FIG. 19 is a front perspective view of droplet generation component 1; FIG. 20 is a back perspective view of droplet generation component 1; FIG. 21 is a top view of droplet generation component 1; FIG. 22 is a bottom view of droplet generation component 1; and FIG. 23, FIG. 24, FIG. 25 and FIG. 26 are side views of droplet generation component 1 in four directions.

Specifically, the droplet generation component 1 comprises a cover plate 2 and at least one annular step 3 connected to the lower surface of the cover plate 2. It should be noted that the annular shape herein represents not only a circular shape. For example, in the embodiment, the outer contour of the annular step 3 is rectangular and the inner contour of the annular step 3 is rounded rectangular. In other embodiments, annular step 3 may also be in other shapes as long as two ends of the step are connected, and the scope of protection of the present invention should not be unduly limited herein.

Specifically, the upper surface of droplet nozzle member 4, the lower surface of cover plate 2 and the annular step 3 together form a droplet generation chamber 36, the droplet nozzles 5 is in communication with the droplet generation chamber 36.

As shown in FIG. 18, the droplet nozzle 5 is provided with a vaporizing part 34 for vaporizing liquid layers of the digital PCR solution in the droplet nozzle 5 and rapidly pushing the liquid layers into droplet generating oil in the droplet generation chamber 36 to generate digital PCR droplets. The volume of the digital PCR droplet to be generated is determined by the volume of the droplet nozzle 5.

As an example, the vaporizing part 34 is arranged on the lower surface or sidewall of droplet nozzle 5, and the vaporizing part 34 comprises a heating element for vaporizing the liquid layers of the digital PCR solution by heating. In the embodiment, the heating element comprises a heating plate, which may either a single metal layer or a composite multilayer metal layer. The shape of vaporizing part 34 comprises, but is not limited to, a round or square shape, and the area thereof may be 0.5 to 2 times the area of the bottom of the droplet nozzle 5. In other embodiments, the vaporizing part 34 may also be arranged on the sidewall of droplet nozzle 5, and the scope of protection of the present invention should not be unduly limited herein.

In the embodiment, the height of annular step 3 is less than twice the diameter of the digital PCR droplets to be generated, so that the obtained digital PCR droplets spread out to form a one-layer structure in the droplet generation chamber 36.

Specifically, as shown in FIG. 21 and FIG. 22, the droplet generation component 1 further comprises at least one droplet generating oil injection hole 6, the droplet generating oil injection hole 6 is in communication with the droplet generation chamber 36 through the cover plate 2. The droplet generation component 1 further comprises at least one exhaust port of the droplet generation chamber 7, the exhaust port 7 of the droplet generation chamber 36 is in communication with the droplet generation chamber 36 through the cover plate 2.

As shown in FIG. 8, the PCR system further comprises at least one PCR reagent chamber 8 for storing the digital PCR solution. As shown in FIG. 17, the droplet nozzle member 4 has flow channels, and the droplet nozzles 5 are in communication with the PCR reagent chamber 8 through the flow channels.

As an example, the flow channels comprise at least one main flow channel 9 and a plurality of branch flow channels 10 connected to the main flow channel 9, and each of the droplet nozzles 5 is connected to one of branch flow channels 10, respectively. FIG. 10 and FIG. 17 display that the droplet nozzle member 4 comprises one main flow channel 9. In other embodiments, the number of the main flow channels 9 may also match the number of the droplet generation chambers 36, and match the number of the annular steps 3. FIG. 20 shows that the droplet generation component 1 comprises an annular step 3. In other embodiments, the number of annular steps 3 may also be plural to construct multiple droplet generation chambers 36.

As an example, materials for constructing the flow channels and the droplet nozzles 5 comprise, but are not limited to, silicon, polymers, photoresists, etc.

Specifically, as shown in FIG. 1 and FIG. 8, the digital PCR system further comprises a substrate 11, the PCR reagent chamber 8 is arranged in substrate 11. As an example, the material for substrate 11 comprises, but is not limited to, any one of transparent or opaque plastics, glass and the substrate 11 may also be metallic.

Figure 27:
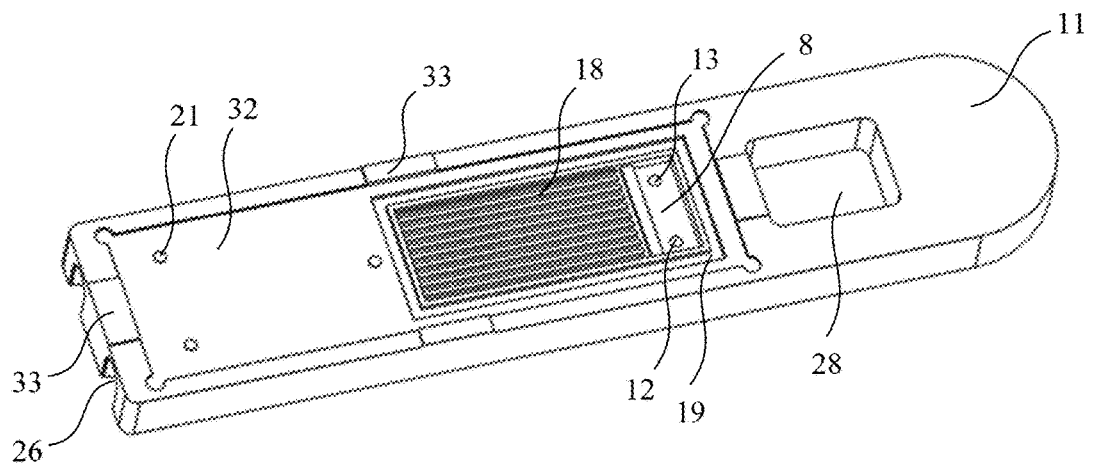
FIG. 27 is a front perspective view of the substrate in the digital PCR system of the present invention.
Figure 28:
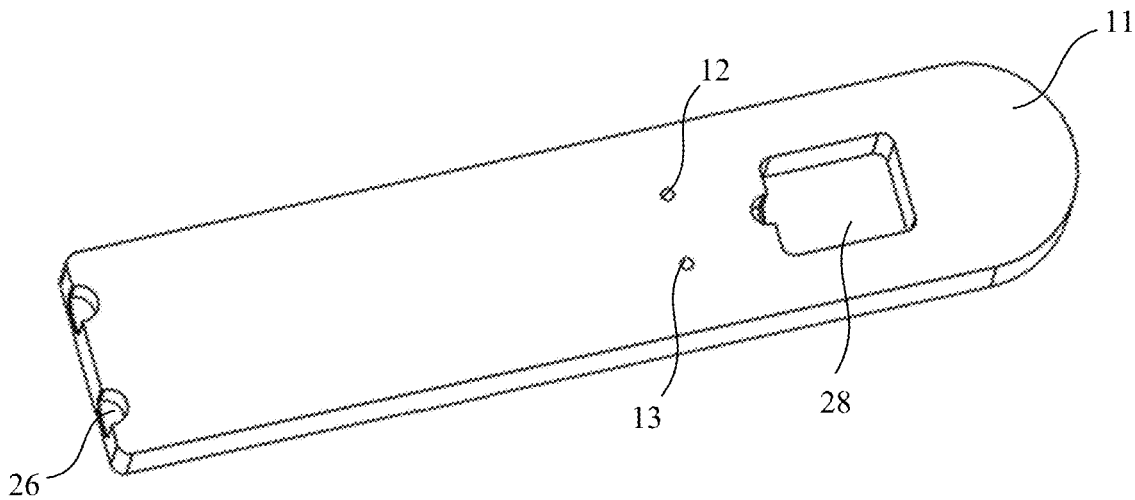
FIG. 28 is a back perspective view of the substrate in the digital PCR system of the present invention.
Figure 29:
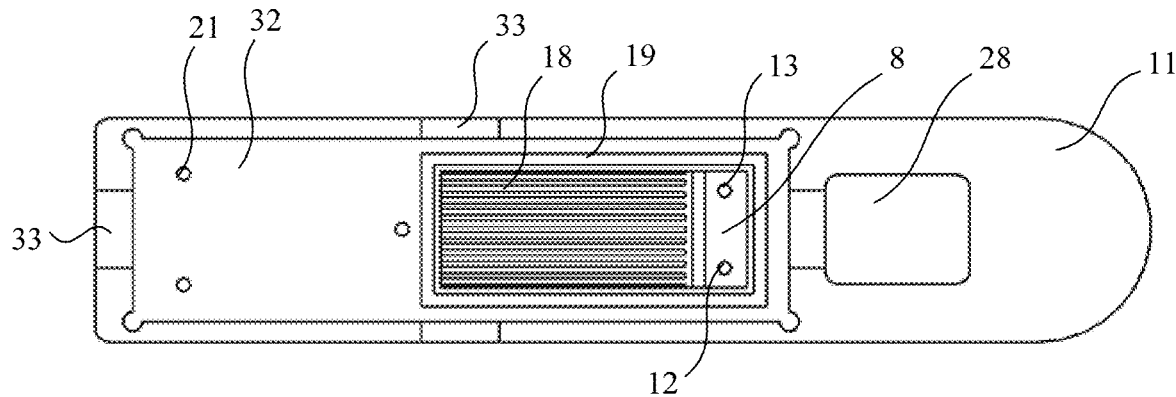
FIG. 29 is a top view of the substrate in the digital PCR system of the present invention.
Figure 30:
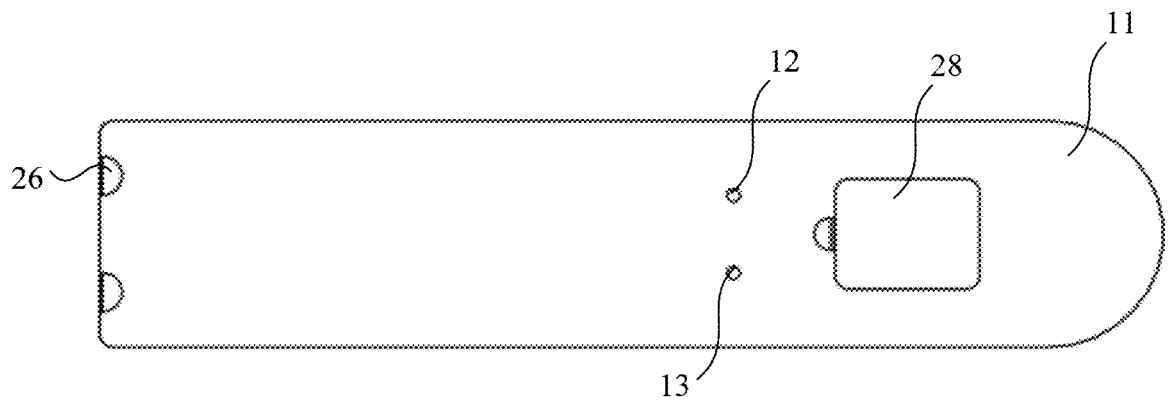
FIG. 30 is a bottom view of the substrate in the digital PCR system of the present invention.
Figure 31:
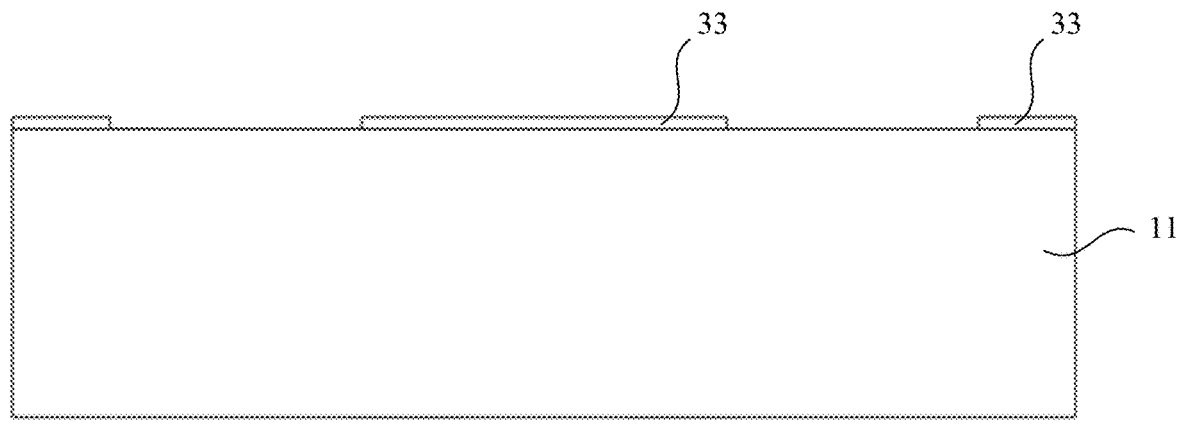
FIG. 31 to FIG. 34 are side views of the substrate in the digital PCR system of the present invention.
Figure 32:
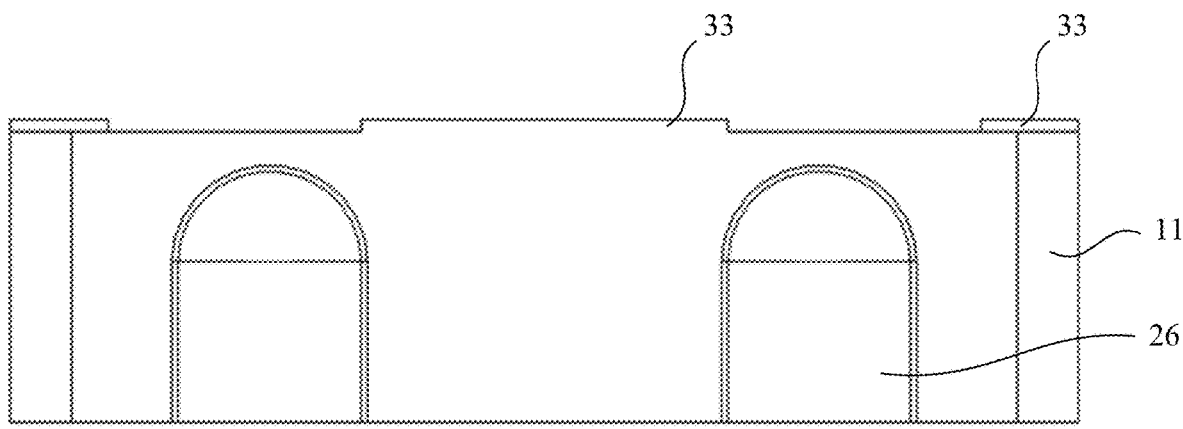
Figure 33:
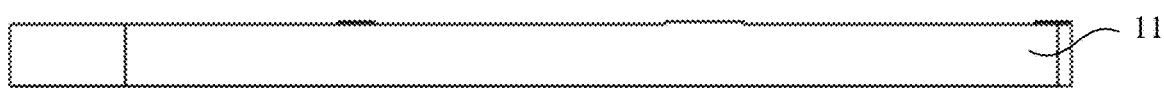
Figure 34:
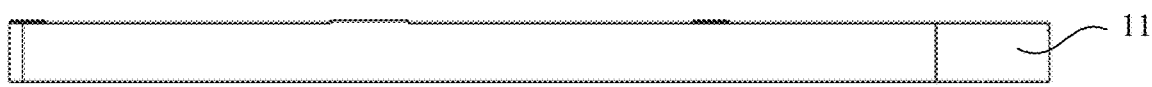

Referring to FIG. 27 to FIG. 34, among them, FIG. 27 is a front perspective view of the substrate; FIG. 28 is a back perspective view of the substrate; FIG. 29 is a upper view of the substrate; FIG. 30 is a bottom view of the substrate, and FIG. 31, FIG. 32, FIG. 33 and FIG. 34 are side views of the substrate in four directions.

Specifically, the PCR reagent chamber 8 has an opening on the upper surface of the substrate 11, and extends towards, but not through, the lower surface of the substrate 11. The droplet nozzle member 4 is connected to the upper surface of the substrate 11, and covers the opening of the PCR reagent chamber.

Specifically, at least one digital PCR solution injection hole 12 is provided on the lower surface of the substrate 11, and digital PCR solution injection hole 12 is in communication with the PCR reagent chamber 8. At least one exhaust port of the PCR reagent chamber 13 is provided on the lower surface of the substrate, and the exhaust port of the PCR reagent chamber 13 is connected to the PCR reagent chamber 8.

Specifically, flexible circuit board 14 is connected above the substrate 11. As an example, the flexible circuit board is fixed on the substrate 11 by gluing (e.g. with double-sided tapes or glue). In the embodiment, the cross-sectional area of droplet nozzle member 4 is larger than the area of the opening of the PCR reagent chamber 8. As shown in FIG. 27 and FIG. 29, at least one channel 18 for preventing glue from flowing to the droplet nozzle member is provided on a surface region of substrate 11 covered by the droplet nozzle member 4. In the present embodiment, the channels 18 are straight, and the number of channels 18 is plural.

As an example, as shown in FIG. 27 and FIG. 29, an annular channel 19 is provided on the surface of the substrate 11 for preventing glue from flowing to the droplet nozzle member, the annular channel is arranged around the droplet nozzle member.

In the present embodiment, a sunken platform 32 is provided on the surface of substrate 11 for accommodating the flexible circuit board, and arc-shaped extended spaces are provided at the four corners of sunken platform 32, and the protrusions 33 around the sunken platform 32 function as a means for positioning when the flexible circuit board is glued to the surface of the sunken platform 32.

As shown in FIG. 10, at least two positioning through holes 20 are arranged in the flexible circuit board 14. As shown in FIG. 29, the positioning bumps 21 at positions corresponding to positioning through holes 20 are provided on the surface of the substrate 11.

Figure 35:
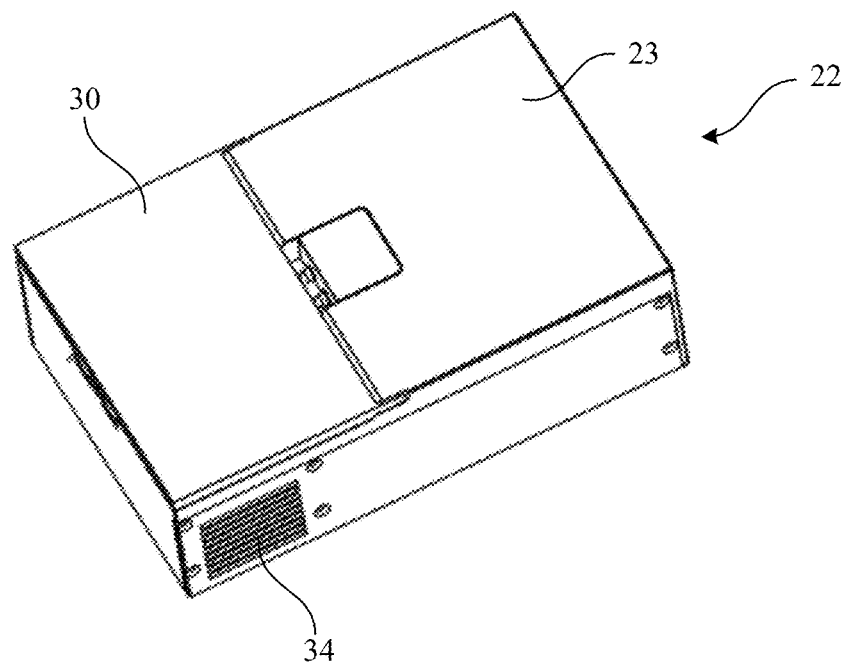
FIG. 35 is a perspective view of the controller in the digital PCR system of the present invention.

Specifically, the digital PCR system further comprises a controller. Referring to FIG. 35, it shows a perspective view of the controller 22, which comprises a controller housing 23 and a controller circuit board arranged in the controller housing (not shown). In the embodiment, controller 22 further comprises a cover 30, cover 30 is connected to the controller housing 22 for covering the substrate 11, and provides a shading environment for PCR reactions.

Figure 36:
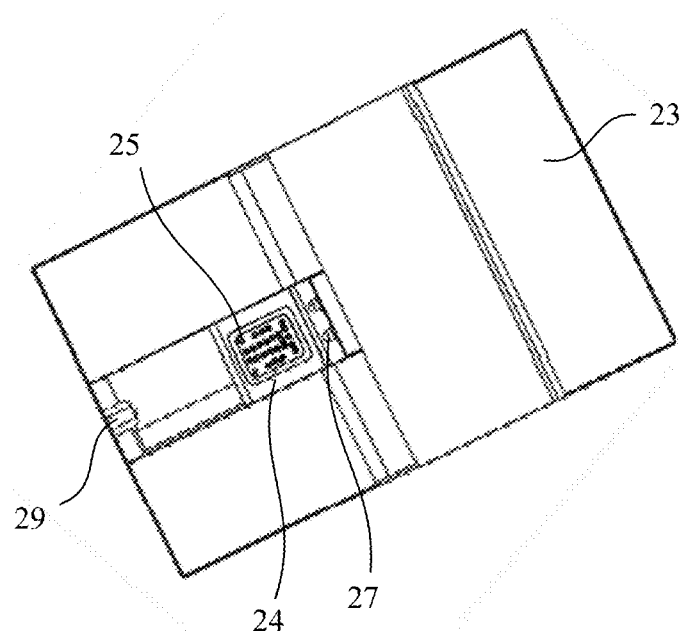
FIG. 36 is a top view of the controller in the digital PCR system of the present invention after the cover is removed.

Referring to FIG. 36, it is a top view of the controller after cover 30 is removed, showing that the controller housing 23 has a support 24 for placing the substrate 11, a plurality of conductive pins for the circuit connection 25 (also known as Pin) connected to the circuit board of the controller are arranged on the surface of the support 24, and the conductive pins for the circuit connection 25 are at positions corresponding to the second connection pads 17.

Figure 37:
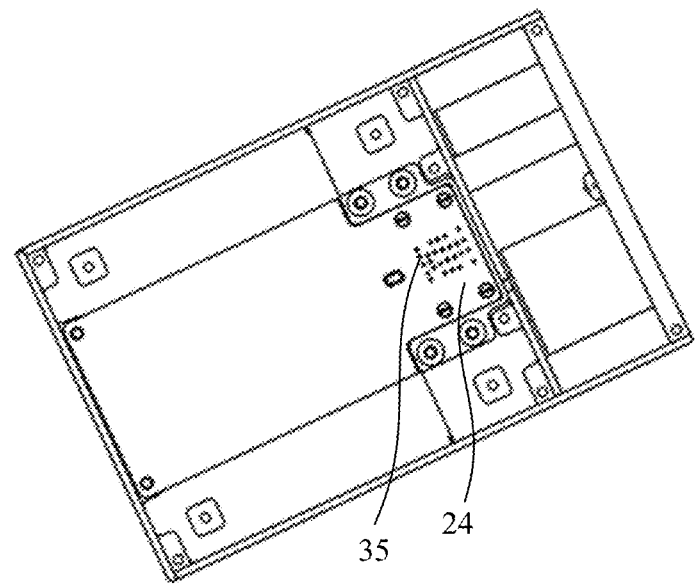
FIG. 37 is a bottom view of the controller in the digital PCR system of the present invention after the controller housing is removed.

Referring to FIG. 37, it is a bottom view of the controller after the controller housing is removed, where a plurality of connection points of the circuit board 35 corresponding to the conductive pins for the circuit connection 25 are provided on the back of the support 24. The circuit board may output signals to conductive pins for circuit connection 25 via connection points of circuit board 35.

Specifically, as shown in FIG. 28, at least one position-limiting slot 26 is provided at one end of substrate 11, and as shown in FIG. 36, at least one position-limiting part 29 corresponding to position-limiting slot 26 is provided in the controller housing 23.

Specifically, as shown in FIG. 28, a position-limiting through hole 28 is provided in the substrate 11, the position-limiting through hole 28 penetrates the front surface and the back surface of the substrate, and as shown in FIG. 36, a position-limiting part 29 corresponding to the position-limiting through hole 28 is provided in the controller housing 23.

Specifically, the digital PCR system further comprises a heating module for heating the droplet generation chamber 36, in order to provide reaction conditions at a specific temperature. As an example, the heating module is integrated in the droplet nozzle member 4.

Specifically, the digital PCR system also comprises a temperature sensor for measuring the temperature in the droplet generation chamber 36, in order to monitor the temperature in the droplet generation chamber 36. As an example, the temperature sensor is integrated in droplet nozzle member 4.

Figure 38:
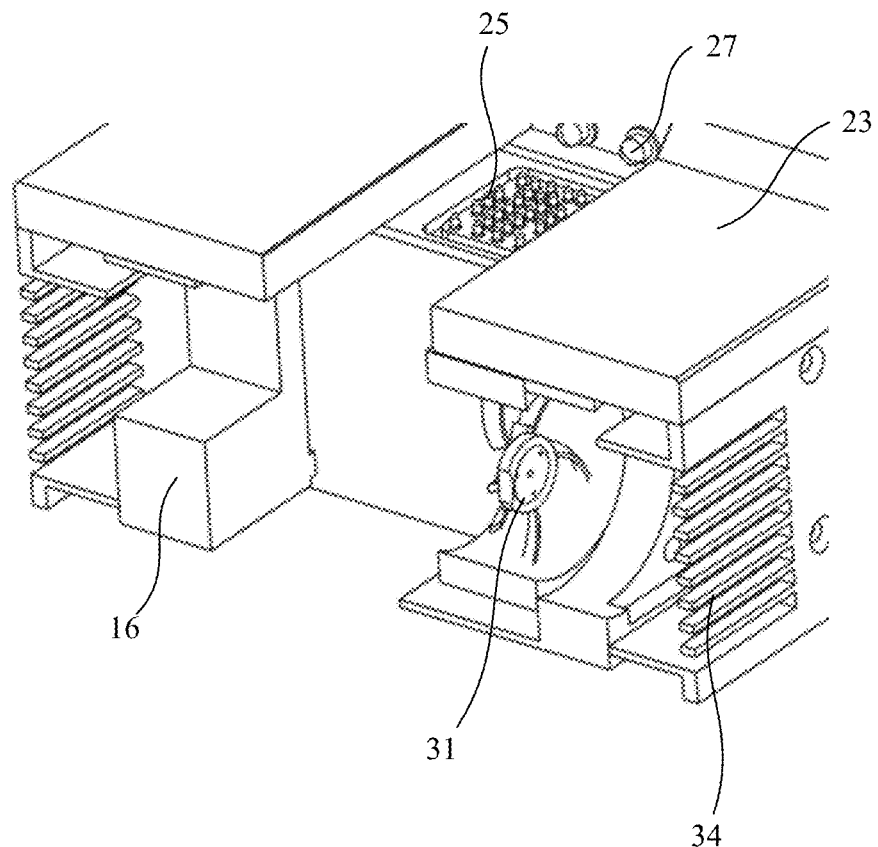
FIG. 38 is a schematic of an external cooling fan arranged in the controller housing in the digital PCR system of the present invention.

Specifically, the digital PCR system further comprises an external cooling fan for cooling the droplet generation chamber 36. As an example, the external cooling fan is arranged in controller housing 23. Referring to FIG. 38, it is a schematic of external cooling fan 31 arranged in controller housing 23, and further a vent 34 arranged close to external cooling fan 31. FIG. 38 also shows a housing supporting structure 16.

Specifically, the external cooling fan may also be replaced by an external thermoelectric cooler. A thermoelectric cooler (TEC) is produced based on the Peltier effect of semiconductor materials. The so-called Peltier effect is the phenomenon that when DC current is applied across a couple composed of two semiconductor materials, one side absorbs heat and the other side emits heat. The heavily doped N-type and P-type bismuth tellurides are mainly used as semiconductor materials for TECs, and the bismuth telluride elements are electrically connected in series and thermally in parallel. TECs comprise a number of P-type and N-type pairs (groups) that are connected together by electrodes and sandwiched between two ceramic electrodes. When electric current flows through a TEC, heat generated by the current is transferred from one side of the TEC to the other, thereby creating a "hot" side and a "cold" side in the TEC, which is heating and cooling principle of TEC.

Furthermore, the digital PCR system further comprises an optical detection system for PCR signal collection and detection without transferring samples. The main parts of the optical system comprise: a fluorescent light source, a brightfield light source, control circuits, a lens group for optical amplification, a fluorescent filter, a CCD camera, a slide system for moving lens, and a housing for shading. The photographic area of the optical system is the entire area of the cover plate. It may be one shot or multiple shots merged together.

The digital PCR system of the present invention can be used for generating digital PCR droplets. The rapid droplet generation relies on the instantaneous vaporization of liquid layers with a thickness in nanometer-scale by using vaporizing parts in droplet nozzles, so the digital PCR solution inside the droplet nozzles is rapidly pushed into droplet generating oil to generate digital PCR droplets. Compared with the generation rate of 100 droplets per second on the market, a droplet generation rate of more than 1000 drops per second can be achieved by the droplet generation technique of the present invention. Compared with the method by which the oil and water phases move together to generate droplets, the oil phase in the technical solution of the present invention is static, so the consumption of oil is greatly reduced, thus reducing the amount of oil by about 50%. The technical solution of the present invention has an efficient utilization rate of digital PCR oil. Because of the precise temperature control integrated on the silicon-based droplet nozzle member or thermal bubble printing chips, in situ temperature-controlled PCR is realized. And the integrated optical system allows detection without transferring samples. This not only reduces the operation time, but also improves the accuracy of detection by reducing human error. In situ digital PCR droplets may spread out to form a layer.

Embodiment 2

The present invention also provides a method for generating digital PCR droplets, comprising the following steps of: the digital PCR solution is vaporized by using vaporizing parts and rapidly pushed into droplet generating oil to generate digital PCR droplets.

As an example, the thermal bubble technique is used for high-speed digital PCR droplet generation. The vaporizing parts comprise heating elements for vaporizing the liquid layers of the digital PCR solution by heating.

Specifically, the generation rate of the digital PCR droplets is controlled by controlling the heating time, the number of heatings and the time intervals of heating of the heating element. The digital PCR droplet generation at a rate of more than 1000 droplets per second can be achieved by the method for generating digital PCR droplets of the present invention.

As an example, the method for generating digital PCR droplets comprises the following steps of:
S1: injecting digital PCR solution into a PCR reagent chamber, so that the digital PCR solution enters the droplet nozzles in communication with the PCR reagent chamber to form liquid layers of the digital PCR solution;
S2: adding droplet generating oil into a droplet generation chamber;
S3: the liquid layers are vaporized by using the vaporizing parts and rapidly pushed into the droplet generating oil in the droplet generation chamber to generate the digital PCR droplets.

Specifically, the thicknesses of the liquid layers are in nanometer scale, and larger than 0.2 nm. In the embodiment, the thickness of the liquid layers is in the range from 0.2 nm to 30,000 nm.

Specifically, the height of the droplet generation chamber is less than twice the diameter of digital PCR droplets to be generated, so that the obtained digital PCR droplets spread out to form a layer in the droplet generation chamber.

Specifically, after the digital PCR solution in the PCR reagent chamber is completely pushed into the droplet generation chamber to generate digital PCR droplets, the PCR reagent chamber is filled with droplet generating oil, so that the PCR reagent chamber is kept filled to prevent the generated droplets from returning to the PCR reagent chamber. Subsequently, seals can be used to seal the droplet generating oil injection hole and the exhaust port of the droplet generation chamber on the wall of the droplet generation chamber, and the digital PCR solution injection hole and the exhaust port of the PCR reagent chamber on the wall of the PCR reagent chamber. The seals comprise, but are not limited to, rubber plugs, parafilm, rubber rings, gasket seals, etc. The seals may be made of soft plastic materials such as rubber, PDMS.

Specifically, after the above-mentioned sealing, in situ temperature-controlled PCR can be realized by using the integrated heating module and the temperature sensor in the droplet nozzle member (which may be thermal bubble print chips) and an external fan to control the rise or fall of temperature required for PCR. Thermoelectric cooling film may also replace the fan for cooling based on the specific temperature requirements.

Specifically, the integrated optical system may also be used to collect and detect PCR signals without transferring the sample.

Figure 39:
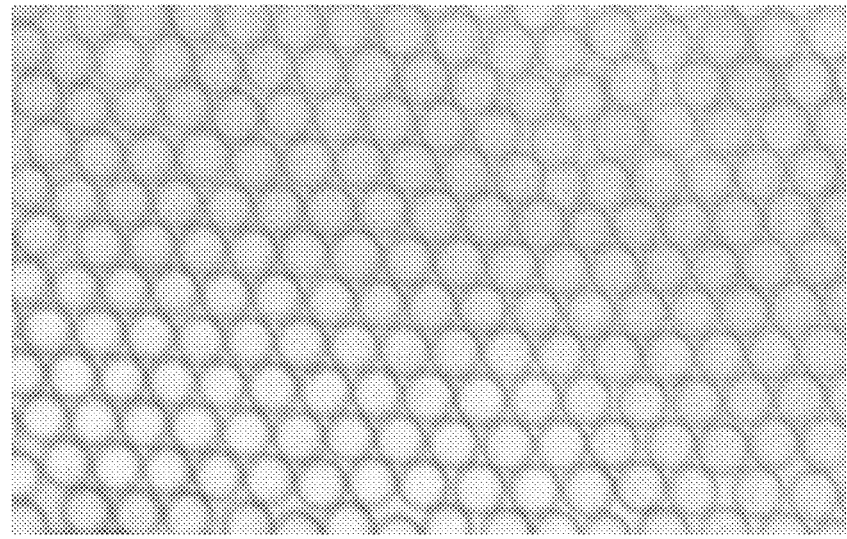
FIG. 39 is an optical microscope image of the digital PCR droplets generated by using the digital PCR system of the present invention.

Referring to FIG. 39, it is an optical microscope image of the digital PCR droplets generated by using the digital PCR system of the present invention, showing that the profile of the generated digital PCR droplets are symmetric and uniform.

Figure 40:
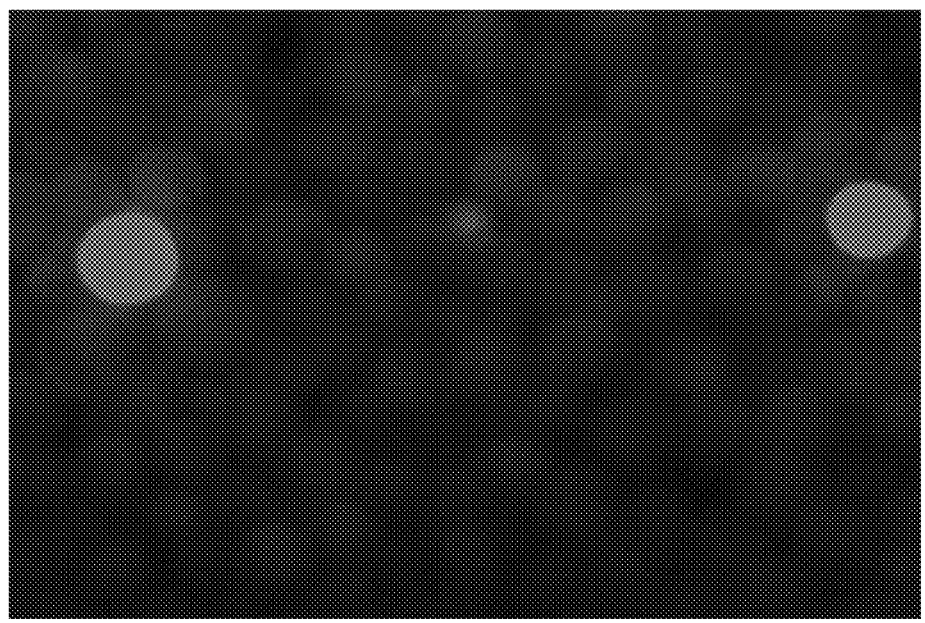
FIG. 40 is a fluorescence image of the digital PCR droplets generated by using the digital PCR system of the present invention.

After generating droplets by using standard digital PCR, the positive droplets with fluorescent signals can be observed after 40 cycles of in situ conventional PCR temperature-controlled reaction. Referring to FIG. 40, it shows a fluorescence image of the digital PCR droplets generated by using the digital PCR system of the present invention All of digital PCR biochemical reagents can be utilized when using the digital PCR system and the method for generating digital PCR droplets of the present invention. The concentrations of many biomarker molecules in the blood are very low (e.g., circulating tumor DNA has only 3 DNA molecules per 2 ml of blood), but the digital PCR system and the method for generating digital PCR droplets of the present invention have the characteristic that the number of droplets generated is not limited by the amount of oil used, and have the feature of high speed, thus enabling the application of digital PCR in such detection.

In conclusion, thermal bubble technique is used in the digital PCR system and the method for generating digital PCR droplets of the present invention for high-speed digital PCR droplet generation. The rapid droplet generation relies on the instantaneous heating and vaporization of liquid layers with a thickness in nanometer-scale by using vaporizing parts in droplet nozzles, so digital PCR solution inside the droplet nozzles is quickly pushed into droplet generating oil to generate digital PCR droplets. Compared with the generation speed of 100 droplets per second on the market, a droplet generation speed of more than 1000 drops per second can be achieved by the droplet generation technique of the present invention. Compared with the method by which the oil and water phases move together to generate droplets, the oil phase in the technical solution of the present invention is static, so the consumption of oil is greatly reduced, reducing the amount of oil by about 50%. Because of the precise temperature control integrated on the silicon-based droplet nozzle member or thermal bubble printing chips, in situ temperature-controlled PCR is realized. And the integrated optical system allows detection without transferring samples. This not only reduces the operation time, but also improves the accuracy of detection by reducing human error. In situ digital PCR droplets may spread out to form a layer. Therefore, the present invention effectively overcomes various shortcomings in the prior art and has a high utility value in industry.

The above-mentioned embodiments only illustrate the principle and efficacy of the present invention, and are not intended to limit the present invention. The above embodiments may be modified or altered by any person skilled in the art without departing from the spirit and scope of the present invention. Therefore, all equivalent modifications or alterations made by those with ordinary knowledge in the technical field, without departing from the spirit and technical ideas disclosed in the present invention, should still be covered by the claims of the present invention.

The invention claimed is:

1. A digital polymerase chain reaction (PCR) system, comprising:

a droplet generation component, comprising a cover plate and at least one annular step connected to a lower surface of said cover plate; and a droplet nozzle member, connected to a bottom of the droplet generation component, and comprising a plurality of droplet nozzles, said plurality of droplet nozzles has openings on a upper surface of said droplet nozzle member, said plurality of droplet nozzles extends toward, but not through, a lower surface of said droplet nozzle member, wherein the upper surface of the droplet nozzle member, the lower surface of the cover plate and the annular step together form a droplet generation chamber, said plurality of droplet nozzles are connected to said droplet generation chamber, and each of said plurality of droplet nozzles have a single vaporizing part for vaporizing digital PCR solution inside said plurality of droplet nozzles, and generate a vapor of digital PCR solution into droplet generating oil in said droplet generation chamber to generate digital PCR droplets at a rate of more than 1000 droplets per second, and wherein said droplet nozzle member comprises a thermal bubble print chip.

2. The digital PCR system of claim 1, wherein a height of said annular step is less than twice a diameter of the generated digital PCR droplets, so that the generated digital PCR droplets spread out to form a one-layer structure in said droplet generation chamber.

3. The digital PCR system of claim 1, wherein said droplet generation component further comprises at least one droplet generating oil injection hole, said at least one droplet generating oil injection hole is connected to said droplet generation chamber through said cover plate.

4. The digital PCR system of claim 1, wherein said droplet generation component further comprises at least one exhaust port of droplet generation chamber, said at least one exhaust port of droplet generation chamber is connected to said droplet generation chamber through said cover plate.

5. The digital PCR system of claim 1, wherein the single vaporizing part of each of said plurality of droplet nozzles is on a lower surface of each respective droplet nozzle of the plurality of droplet nozzles.

6. The digital PCR system of claim 1, wherein each of said plurality of droplet nozzles comprises an opening that has a cross-sectional shape that is round, ellipse, or polygon.

7. The digital PCR system of claim 1, wherein each respective single vaporizing part comprises a heating element for vaporizing liquid layers of said digital PCR solution by heating.

8. The digital PCR system of claim 7, wherein said heating elements comprise at least one metal layer.

9. The digital PCR system of claim 1, wherein said PCR system further comprises at least one PCR reagent chamber for storing the digital PCR solution, said droplet nozzle member has a flow channel, and said plurality of droplet nozzles are connected to said at least one PCR reagent chamber through said flow channel.

10. The digital PCR system of claim 9, wherein said flow channel comprise at least one main flow channel and a plurality of branch flow channels connecting to said at least one main flow channel, and each of said plurality of droplet nozzles is connected to one of said plurality of branch flow channels.

11. The digital PCR system of claim 9, wherein said digital PCR system further comprises a substrate, said at least one PCR reagent chamber is disposed in said substrate and has an opening an upper surface of said substrate, and said droplet nozzle member is connected to the upper surface of said substrate and covers the opening of said at least one PCR reagent chamber.

12. The digital PCR system of claim 11, wherein at least one digital PCR solution injection hole is provided in a lower surface of said substrate, said digital PCR solution injection hole being connected to said at least one PCR reagent chamber.

13. The digital PCR system of claim 11, wherein at least one exhaust port of the PCR reagent chamber is provided on a lower surface of said substrate, said exhaust port of PCR reagent chamber is connected to said at least one PCR reagent chamber.

14. The digital PCR system of claim 11, wherein said digital PCR system further comprises a flexible circuit board, said flexible circuit board is connected from above and to the substrate, said flexible circuit board has a through hole for accommodating said droplet nozzle member.

15. The digital PCR system of claim 14, wherein said flexible circuit board is connected to said substrate by a glue.

16. The digital PCR system of claim 15, wherein a cross-sectional area of said droplet generation component is larger than a cross-sectional area of the opening of said at least one PCR reagent chamber, at least one channel for preventing the glue from flowing to said droplet nozzle member is provided on a region of said substrate surface covered by said droplet nozzle member.

17. The digital PCR system of claim 15, wherein an annular channel is provided on the upper surface of said substrate for preventing the glue from flowing to said droplet nozzle member, said annular channel is arranged around said droplet nozzle member.

18. The digital PCR system of claim 14, wherein further comprising at least two positioning through holes arranged in said flexible circuit board, and positioning bumps at positions corresponding to the at least two positioning holes are provided on the upper surface of said substrate.

* * * * *